US00RE41633E

(19) United States
(12) Reissued Patent
Zhou et al.

(10) Patent Number: US RE41,633 E
(45) Date of Reissued Patent: Sep. 7, 2010

(54) LIGHT SOURCE FOR SWEPT SOURCE OPTICAL COHERENCE TOMOGRAPHY BASED ON CASCADED DISTRIBUTED FEEDBACK LASERS WITH ENGINEERED BAND GAPS

(75) Inventors: Yan Zhou, Pleasanton, CA (US); Keith E. O'Hara, San Ramon, CA (US)

(73) Assignee: Carl Zeiss Meditec, Inc., Dublin, CA (US)

(21) Appl. No.: 12/555,622

(22) Filed: Sep. 8, 2009

Related U.S. Patent Documents

Reissue of:
(64) Patent No.: 7,554,668
Issued: Jun. 30, 2009
Appl. No.: 11/503,046
Filed: Aug. 11, 2006

U.S. Applications:
(60) Provisional application No. 60/714,286, filed on Sep. 6, 2005.

(51) Int. Cl.
*G01B 9/02* (2006.01)
*G01B 11/02* (2006.01)

(52) U.S. Cl. ..... 356/479; 356/497
(58) Field of Classification Search ..... 356/479, 356/497
See application file for complete search history.

(56) References Cited

U.S. PATENT DOCUMENTS

| | | | | |
|---|---|---|---|---|
| 7,079,718 | B2 * | 7/2006 | Welch et al. | 385/14 |
| 7,391,520 | B2 * | 6/2008 | Zhou et al. | 356/479 |
| 2005/0014300 | A1 * | 1/2005 | Welch et al. | 438/17 |
| 2007/0002327 | A1 * | 1/2007 | Zhou et al. | 356/497 |

OTHER PUBLICATIONS

T. Amano et al., "Optical frequency–domain reflectometry with a rapid wavelength–scanning superstructure–grating distributed Bragg reflector laser," *Applied Optics,* vol. 44, No. 5, Feb. 10, 2005, pp. 808–816.

T. Van Caenegem et al., "Selective Area Growth on Planar Masked InP Substrates by Metal Organic Vapour Phase Epitaxy (MOVPE)," *Prog. Crystal Growth and Charact.,* vol. 35 (1997), No. 2–4, pp. 263–288.

M.A. Choma et al., "Sensitivity advantage of swept source and Fourier domain optical coherence tomography," *Optics Express,* vol. 11, No. 18, Sep. 8, 2003, pp. 2183–2189.

J. Hong et al., "Enhanced Wavelength Tuning Range in Two–Section Complex–Coupled DFB Lasers by Alternating Gain and Loss Coupling," *Journal of Lightwave Technology,* vol. 16, No. 7, Jul. 1998, pp. 1323–1328.

J. Hong et al., "Matrix–Grating Strongly Gain–Coupled (MG–SGC) DFB Lasers with 34–nm Continuous Wavelength Tuning Range," *IEEE Photonics Technology Letters,* vol. 11, No. 5, May 1999, pp. 515–517.

(Continued)

*Primary Examiner*—Patrick J Connolly
(74) *Attorney, Agent, or Firm*—Morrison & Foerster LLP

(57) ABSTRACT

The present invention is a tunable semiconductor laser for swept source optical coherence tomography, comprising a semiconductor substrate; a waveguide on top of said substrate with multiple sections of different band gap engineered multiple quantum wells (MQWs); a multiple of distributed feedback (DFB) gratings corresponding to each said band gap engineered MWQs, each DFB having a different Bragg grating period; and anti-reflection (AR) coating deposited on at least the laser emission facet of the laser to suppress the resonance of Fabry-Perot cavity modes. Each DFB MQWs section can be activated and tuned to lase across a fraction of the overall bandwidth as is achievable for a single DFB laser and all sections can be sequentially activated and tuned so as to collectively cover a broad bandwidth, or simultaneously activated and tuned to enable a tunable multi-wavelength laser. The laser hence can emit either a single lasing wavelength or a multiple of lasing wavelengths and is very suitable for swept-source OCT applications.

8 Claims, 6 Drawing Sheets

OTHER PUBLICATIONS

J. Hong et al., "Cascaded Strongly Gain–Coupled (SGC) DFB Lasers with 15–nm Continuous–Wavelength Tuning," *IEEE Photonics Technology Letters,* vol. 11, No. 10, Oct. 1999, pp. 1214–1216.

R. Huber et al., "Three–dimenional and C–mode OCT imaging with a compact, frequency swept laser source at 1300 nm," *Optics Express,* vol. 13, No. 26, Dec. 26, 2005, pp. 10523–10529.

R. Huber et al., "Fourier Domain Mode Locking (FDML): A new laser operating regime and applications for optical coherence tomography," *Optics Express,* vol. 14, No. 8, Apr. 17, 2006, pp. 3225–3237.

T. Mitsui, "Dynamic Range of Optical Reflectometry with Spectral Interferometry," *Jpn. J. Appl. Phys.,* vol. 38, Pt. 1, No. 10, Oct. 1999, pp. 6133–6137.

M. Müller ller et al., "1.3–μm Continuously Tunable Distributed Feedback Laser With Constant Power Output Based on GaInNAs–GaAs," *IEEE Photonics Technology Letters,* vol. 15, No. 7, Jul. 2003, pp. 897–899.

B. Pezeshki, "New approaches to laser tuning," *Optics & Photonics News,* May 2001, pp. 34–38.

Catalogue/Brochure, "Optical Coherence Tomography," by ThorLabs, Jan. 2006, 13 pages in length.

* cited by examiner

LIGHT SOURCE FOR SWEPT SOURCE OPTICAL COHERENCE TOMOGRAPHY BASED ON CASCADED DISTRIBUTED FEEDBACK LASERS WITH ENGINEERED BAND GAPS

Matter enclosed in heavy brackets [ ] appears in the original patent but forms no part of this reissue specification; matter printed in italics indicates the additions made by reissue.

*PRIORITY*

*This application claims the benefit of the filing date under 35 U.S.C. §119(e) of U.S. Provisional Patent Application Ser. No. 60/714,286, filed Sep. 6, 2005, which is hereby incorporated by reference in its entirety.*

TECHNICAL FIELD OF THE INVENTION

One or more embodiments of the present invention relate generally to light sources for optical imaging. In particular, the invention is a semiconductor-based tunable laser for swept source optical coherence tomography.

BACKGROUND OF THE INVENTION

Optical Coherence Tomography (OCT) is a technology for performing high-resolution cross sectional imaging that can provide images of tissue structure on the micron scale in situ and in real time (U.S. Pat. No. 5,321,501). In recent years, it has been demonstrated that Fourier domain OCT (FD-OCT), which so far employs either a wavelength swept source and a single detector or a broadband source and an array spectrometer, has significant advantages in both speed and signal-to-noise ratio as compared to time domain OCT (TD-OCT) (Choma, M. A. et al. (2003). "Sensitivity advantage of swept source and Fourier domain optical coherence tomography." Optics Express 11(18): 2183-2189). In TD-OCT, the optical path length between the sample and reference arms needs to be mechanically scanned. In both swept source OCT (SS-OCT) and spectrometer-based spectral domain OCT (SD-OCT), the optical path length difference between the sample and reference arm is not mechanically scanned. Instead, a full axial scan (also called A-scan) is obtained in parallel for all points along the sample axial line within a short time determined by the wavelength sweep rate of the swept source (in SS-OCT) or the line scan rate of the line scan camera (in SD-OCT). As a result, the speed for each axial scan can be substantially increased as compared to the mechanical scanning speed of TD-OCT and this is especially beneficial for real-time imaging of living biological samples such as the human eye. In addition, SD-OCT and SS-OCT can provide substantially greater signal-to-noise ratio relative to TD-OCT, as explained by Mitsui (1999) "Dynamic Range of Optical Reflectometry with Spectral Interferometry." Japanese Journal of Applied Physics 38(10): 6133-6137.

SS-OCT can be achieved using either a single lasing wavelength tunable laser or a multiple lasing wavelengths tunable laser. FIG. 1 shows the basic configuration of a SS-OCT system based on a tunable laser with a single lasing wavelength. Light from a tunable single-wavelength laser 102 is split through a beam splitter or fiber coupler 104 into a reference arm 106 and a sample arm 108 of an interferometer and the interference signal is detected with a single high-speed photodetector 110. By sweeping the wavelength of the monochromatic source 102, the interference spectrum from the OCT interferometer is recorded sequentially. The axial reflectance distribution of the sample is obtained by a Fourier transform of the sequentially acquired spectral interference signal.

FIG. 2 shows a system, described in a co-pending US patent application by Zhou and Everett ("Fourier domain optical coherence tomography employing a swept multi-wavelength laser and a multi-channel receiver" filed on Jul. 1, 2005, application Ser. No. 11/174,158) incorporated herein by reference, of a SS-OCT system based on a tunable laser with multiple lasing wavelengths. Light from a tunable multi-wavelength laser 202 is split via a beam splitter, for example, fiber coupler 204, into a reference arm 206 and a sample arm 208 of an interferometer. Light returning from the reference arm and the sample is combined, either with the same splitter as shown in FIG. 2 or another beam combining element as is known in the art of interferometry. The combined, interfered light is sent to a detector, in this case, multi-channel receiver 210. A processor 220 obtains the spectral interferogram data from the multi-channel receiver 210, synchronized with the sweeping of the multi-wavelength laser 202. It combines the data samples from the individual channels to form the full spectral interference fringes and carries out a Fourier transform of the spectral interference fringes to provide the information of the reflectance distribution along the depth within the sample 222.

A practical SS-OCT system requires a high speed swept source with a sweep rate of at least about 20 kHz that is continuously tunable over a broad tuning range (preferably greater than 50 nm). Current commercially available tunable lasers can be divided into electronically tuned lasers and mechanically tuned lasers. Electronically-tuned lasers are either limited in their tuning range (typically 5 nm to 10 nm for a single distributed feedback (DFB) laser), or discretely tunable in order to cover a wider range as in the case of sampled grating distributed feedback reflector (SG-DBR) lasers (see for example, U.S. Pat. No. 4,896,325, U.S. Pat. No. 5,325,392). The discretely tunable lasers described in U.S. Pat. No. 4,896,325 and U.S. Pat. No. 5,325,392 operate using a single gain section, and they tune using a Vernier effect between the two DBR end mirrors, so both DBR end mirrors and a phase-matching device must be simultaneously continuously tuned to produce discrete tuning; these features make this design inconvenient for SS-OCT. Most mechanically tunable lasers are slow. Some use fiber and piezo based Fabry-Perot (FP) filters (see for example Huber, R. et al. (2005) Optics Express 13(9): 3513-3528; and (2006) Optics Express 14(8): 3225-3237) and others use fast rotating polygon mirrors (see for example, US20050035295). For example, patent application US20050035295 and the article by Oh, W. Y. et al. ("Wide tuning range wavelength-swept laser with two semiconductor optical amplifiers." Photonics Technology Letters, IEEE 17(3): 678-680) disclosed a wavelength tuning source for SS-OCT that employs a continuously rotating optical arrangement for lasing wavelength selection. The current price of a swept source suitable for OCT is very high (see for example, Thorlab Inc. Product Catalog, Vol. 17, (2005) page 469) and in addition, the demonstrated wavelength sweep rate is limited to about 20 kHz.

On the other hand, tunable semiconductor lasers developed for optical fiber communications either are step-tuned to fit the ITU grid (see for example, Amano, T. et al. (2005). "Optical frequency-domain reflectometry with a rapid wavelength-scanning superstructure-grating distributed Bragg reflector laser." Applied Optics 44(5): 808-816) or, if continuously tunable, are very slow (see for example, U.S. Pat. No. 6,847,661) and they do not meet the requirement for an SS-OCT system, such as the high wavelength sweeping rate (more than 20 kHz) and the broad spectral range to be covered (e.g. 25 to 200 nm). Although there are various designs of semiconductor based tunable lasers (see for example, Muller, M. et al. (2003) "1.3-μm Continuously Tunable Distributed Feedback Laser With Constant Power Output Based on GaInNAs—GaAs", Photonics Technology Letters, IEEE 15(7) 897-899; Buss J. et al. (2005) "Tunable Laser Diodes and Related Optical Sources" Second Edition, John Wiley & Sons, Inc., Hoboken, N.J., and others as cited in this application, which are all incorporated in their entirety herein by reference), these lasers are not designed specifically for SS-OCT applications. In particular, there are attempts to cascade a few distributed feedback (DFB) semiconductor lasers along a single channel waveguide to achieve complex coupled DFB lasers (see for example, U.S. Pat. No. 5,936,994; U.S. Pat. No. 6,104,739; U.S. Pat. No. 6,201,824; Hong, J. et al. (1998) "Enhanced Wavelength Tuning Range in Two-Section Complex-Coupled DFB Lasers by Alternating Gain and Loss Coupling", Journal of Lightwave Technology, 16(7): 1323). When the individual sections of these lasers are built on semiconductor structures having uniform energy band gap, there is a significant overlap of the optical gain curve associated with each DFB grating and the resulting lasers have limited tuning range.

In light of the above, there is hence a need in the art for a low cost continuously tunable laser that meets the requirement of a real time SS-OCT system.

DETAILED DESCRIPTION

Figure 1:
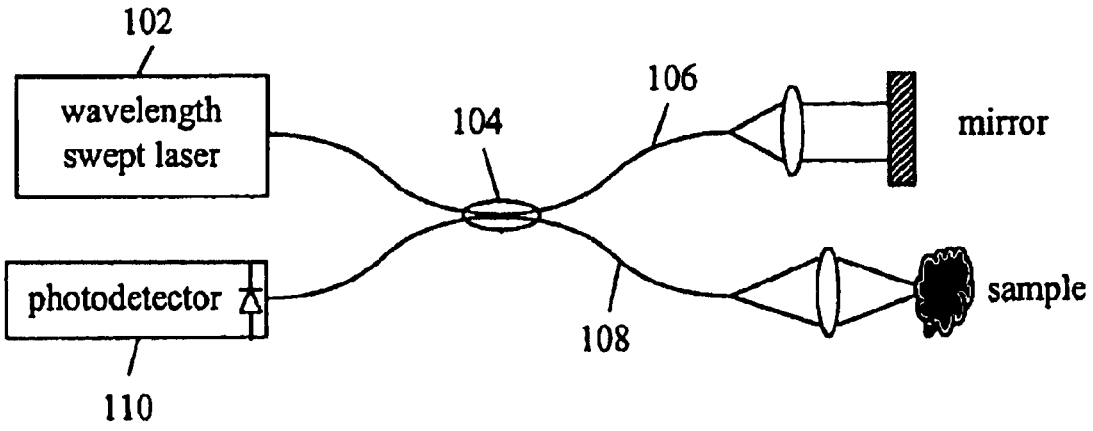
FIG. 1 shows the basic configuration of a SS-OCT system based on a tunable laser with a single lasing wavelength.
Figure 2:
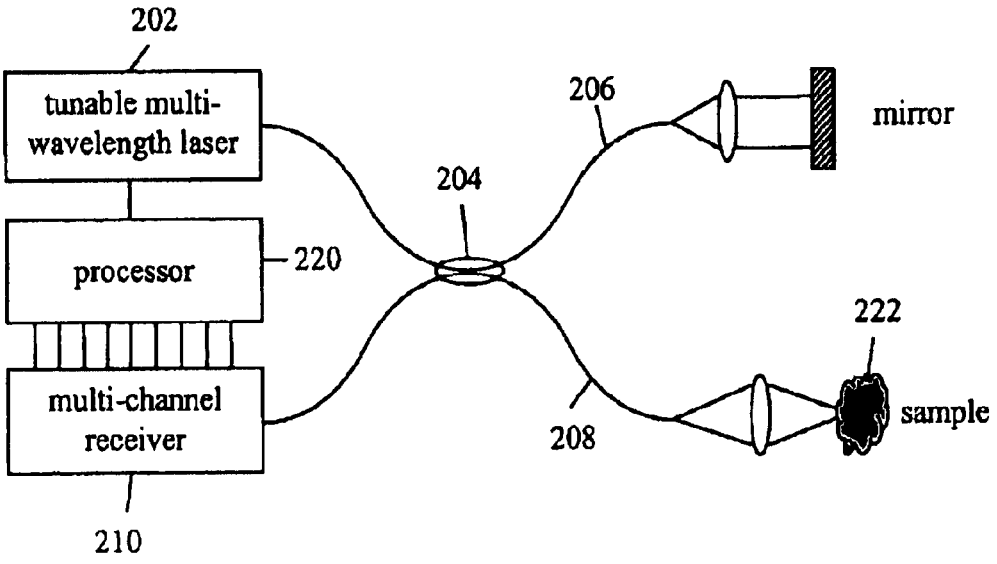
FIG. 2 shows the basic configuration of a SS-OCT system based on a tunable laser with multiple lasing wavelengths.
Figure 2:
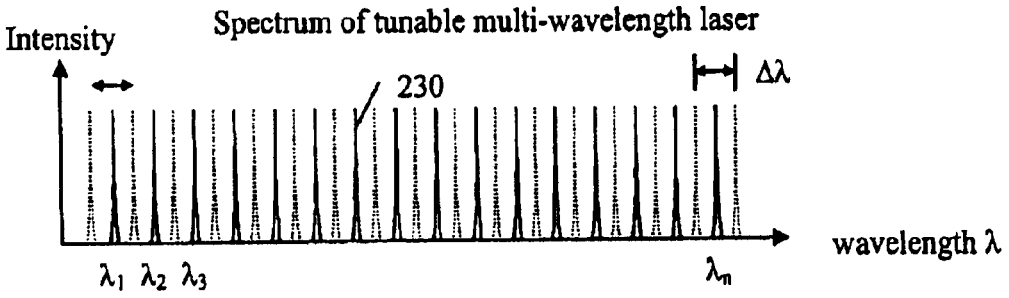
Figure 3:
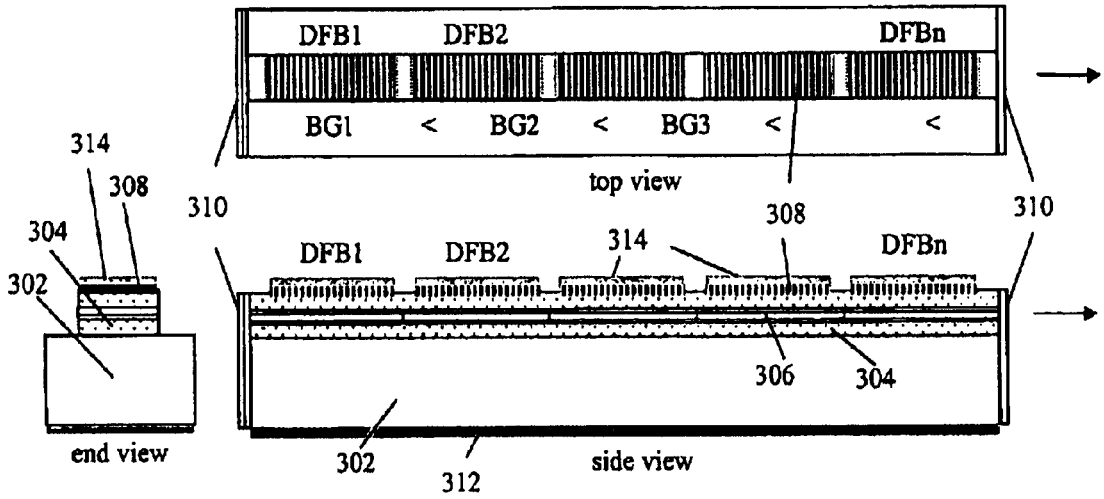
FIG. 3 shows a first embodiment of the design of the invented cascaded multi-DFB based semiconductor band gap engineered laser for swept source OCT.

The present invention is a new design for a widely continuously tunable semiconductor laser that can emit either a single lasing wavelength or multiple lasing wavelengths, which is very suitable for swept-source OCT applications. As shown in FIG. 3, in accordance with one or more embodiments of the present invention, the new design consists of a multiple number of tunable DFB lasers cascaded along a single waveguide with each section of the multiple quantum wells (MQWs) (corresponding to each DFB grating) having a different energy bandgap so that along the laser emission direction, the follow-up sections are significantly transparent to light emitted from the previous sections. Each DFB MQWs section can be activated and tuned to lase across a fraction of the overall bandwidth as is achievable for a single DFB laser and all sections can be sequentially activated and tuned so as to collectively cover a broad bandwidth. MQWs are the preferred gain medium for use in this laser, but any optical gain medium can be used if the wavelength range of gain can be adjusted between individual gain sections. Single quantum wells, semiconductor heterojunctions, or quantum dots are alternative practical gain media. Alternatively, all sections can also be simultaneously activated and tuned to enable a tunable multi-wavelength laser.

The presently invented laser structure can be realized using two well-established technologies. The gain medium with sections of different band gap can be produced by semiconductor band gap engineering through quantum well intermixing (see for example U.S. Pat. No. 6,617,188), or selective area growth or regrowth (see for example T. van Caenegem et al, Progress in Crystal Growth and Characterization of Materials 35(2-4): 263-268). The relatively narrowly-tunable laser resonators are produced using existing DFB laser technology. By cascading a number of tunable DBF lasers along a single waveguide, the cost of such a device can be substantially reduced as compared to that of the mechanically tunable lasers. Although, each DFB laser section can only be tuned over a relatively narrow range (e.g. 5 nm), by sequentially activating and tuning each section, the combined tuning range can hence be greatly increased. (For example, 10 sections can provide a 50 nm tuning range). In addition, the achievable tuning speed can be many orders of magnitude higher than that of the mechanical counterpart.

In a first preferred embodiment of FIG. 3, the laser is made on a semiconductor substrate 302 that has a waveguide 304 with multiple sections of different band-gap-engineered multiple quantum wells (MQWs) 306. The multiple distributed feedback gratings 308 corresponding to the band-gap-engineered MWQs 306 are fabricated either on top of or below the waveguide 304 as shown in FIG. 3, each section has a different Bragg grating period. The quantum well corresponding to each section can have its energy band gap shifted, preferably by a band-gap engineering technique that can be performed after deposition of epitaxial layers of semiconductor; quantum well intermixing is one such post-epi technique. Suppose we use the lasing output on the right hand as shown in the FIG. 3, we can have the peak luminescence wavelengths associated with the different MQW energy band gaps to be $\lambda_1>\lambda_2>\lambda_3> \ldots >\lambda_n$ (from left to right) to avoid re-absorption of emitted laser light from previous sections on the left of each section. Here, the band gap energy of each section increases from left to right. There can be a common bottom cathode electrode 312 electrically connected to the substrate 302 and separate anode electrodes 314 for each section. Each section can be activated and tuned by injecting current which will both pump the gain medium and also tune the effective grating period and hence the lasing wavelength. One can control the rate of current injection in order to vary the carrier densities in the substrate near the Bragg grating, which in turn varies the effective refractive index within the Bragg grating, which in turn creates a variable effective grating period. Alternatively, each section can also be electrically pumped with a constant current and thermally tuned, by respectively injecting a constant electrical current which will pump the gain medium and varying the temperature which will tune the effective grating period and hence the lasing wavelength, although thermal tuning will be much slower as compared to electrical tuning. If there is some degree of overlap of the gain curve between or among some neighboring sections, those follow-up sections in the right hand side portion, closer to the laser emission facet, can be pumped to transparency or to have optical gain but below lasing threshold to ensure that the emitted laser light is not absorbed. Anti-reflection (AR) coating 310 is preferably deposited on at least the laser emission facet or on both facets of the laser to suppress the resonance of Fabry-Perot cavity modes. In this embodiment of FIG. 3, the lasing power may change with the lasing wavelength, but this is acceptable for SS-OCT application because the instantaneous power can be measured and the interference spectrum can be compensated during data processing for the power variation.

Figure 4:
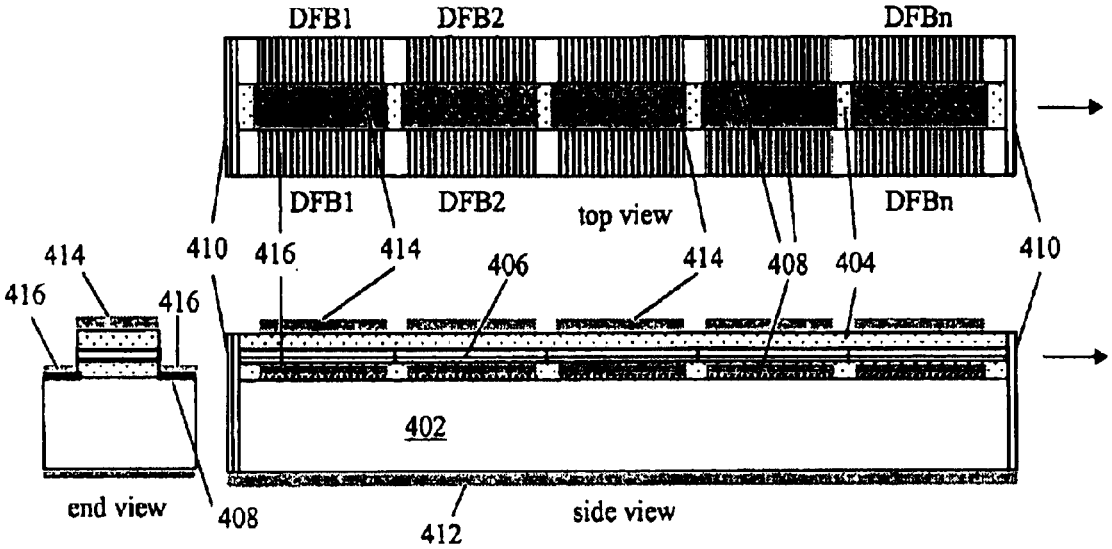
FIG. 4 shows a second embodiment of the design of the invented cascaded multi-DFB based semiconductor band gap engineered laser for swept source OCT.

In a second preferred embodiment as shown in FIG. 4, the distributed feedback structures 408 are made on the two sides of the waveguide 404. Separate electrodes can be used, with the pump electrode 414 on the waveguide 404 for electrically pumping the gain medium, and the other wavelength tuning electrode 416 injecting carriers on the two sides of the waveguide 404 to modulate the refractive index and control the effective grating period. The advantage of this embodiment is that the injection current for laser power control can be substantially separated from the electrical current for lasing wavelength tuning, so that the lasing power can be held substantially constant as the lasing wavelength is tuned. Nearly-constant power gives nearly-uniform signal-to-noise ratio in the interference spectrum, which helps to achieve both good axial resolution and good signal-to-noise ratio in reconstruction of the reflectance distribution. Like the FIG. 3 embodiment, the FIG. 4 embodiment can include a bottom cathode electrode 412 on the substrate 402. In addition, one or both of the ends of the waveguide 406 can include an AR coating 410.

One can have all the sections lase and hence sweep the multiple wavelengths together as a multi-wavelength laser source. In this case, the electrical pumping anode electrodes (314 for embodiment 1 and 414 for embodiment 2) can be made into one anode electrode to reduce the number of electrical connection pins for the laser. On the other hand, one can turn the sections on one at a time, sweeping each section for simple detection. In the latter case, for the second preferred embodiment, the wavelength tuning electrode 416 can be combined to one for all the gratings to reduce the electrode number, while each pumping electrode needs to be activated sequentially.

Suppose we have 20 sections, with each section 500 μm long, the output lasing power from each section can reach 10 to 40 mW and the complete laser die is 10 mm long which is feasible.

Figure 5:
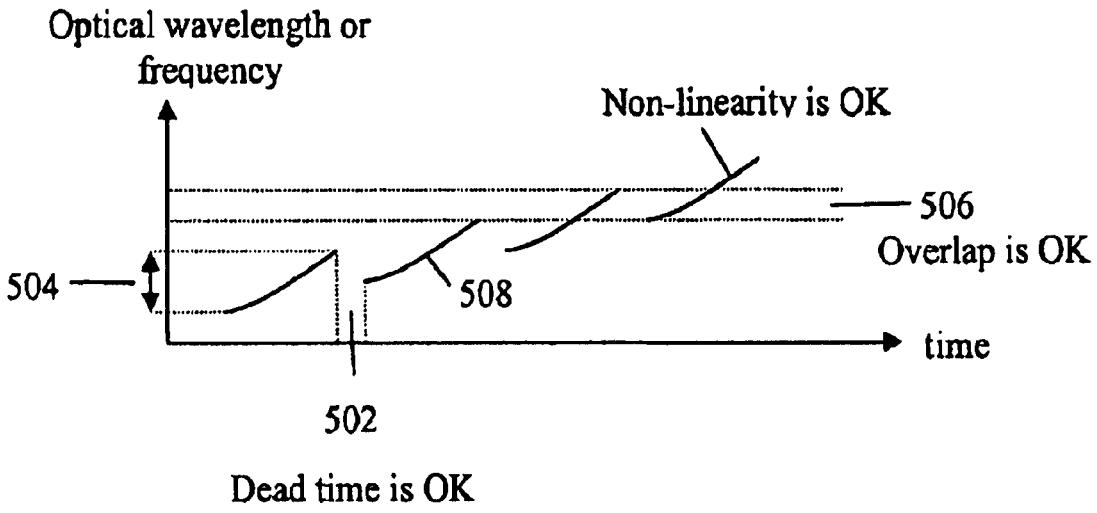
FIG. 5 shows the flexibility of the relationship between the tunable lasing wavelength(s) and the tuning time.

Note that there can be dead time 502 between turning one section off and turning the next section on as is shown in FIG. 5, but this is acceptable as long as we know the lasing wavelength and power at a specific time, because we can use data processing to drop the signal during the dead time 502. The tuning range 504 of each section can also overlap with that of the next section, as we can use data processing to drop or average the measurements in the duplicated or overlapped wavelength range 506. The tuning curve 508 also does not need to be linear, as long as we know the shape, we can compensate it in data processing.

Often one uses an auxiliary interferometer to monitor the wavelength sweep (for example, FIG. 5 of U.S. Pat. No. 5,956,355). Often the auxiliary interferometer is a Fabry-Perot etalon that provides a series of peaks in transmitted power, these peaks being uniformly spaced in inverse wavelength. In this multiple-section laser, the first transmission peak traversed by each section must be identified from among the many transmission peaks of the auxiliary interferometer. The relationship of wavelength $\lambda$ versus time t of each section may be stable enough such that the identity of the first peak of a given section can be determined once by a wavelength measurement during initial calibration. If the sweep relationship is not that stable, one can use a second auxiliary interferometer with a different spacing of transmission peaks to uniquely identify the starting wavelength of each section based on its relationship to two incommensurate sets of transmission peaks.

Figure 6:
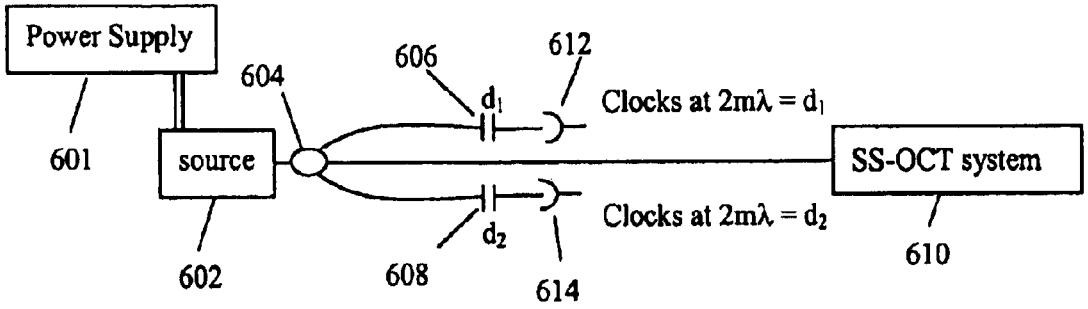
FIG. 6 shows a scheme to monitor the lasing wavelength(s) so that the lasing wavelength versus time relationship can be calibrated in real time.

FIG. 6 shows such a scheme to monitor the light source so that the lasing wavelength versus time relationship can be calibrated in real time. The tunable light source 602 is powered by electrical power source 601 and linked to the OCT system 610 through, for example, a fiber. A small fraction of light is tapped by fiber coupler 604 to Fabry-Perot filters 606 and 608, these filters having etalon optical gaps of $d_1$ and $d_2$ respectively. The optical power transmitted through filters 606 and 608 can be measured by photodetectors 612 and 614 respectively. Each Fabry-Perot etalon will provide a series of peaks in transmitted power, but the spacing of these peaks differs for filters 606 and 608 due to their different gap spacing. The combined pattern of transmission from both filters can be used to uniquely identify the wavelength of a given transmission peak, and thus to determine the wavelength of the swept source 602.

The presently invented tunable semiconductor laser source is especially useful for SS-OCT applications. Meanwhile, the presently invented light source is also useful for other applications including sensing, spectroscopy and metrology.

Although various embodiments that incorporate the teachings of the present invention have been shown and described in detail herein, those skilled in the art can readily devise many other varied embodiments that still incorporate these teachings.

The following references are hereby incorporated by reference.

US Patent Documents

U.S. Pat. No. 4,896,325
U.S. Pat. No. 5,321,501
U.S. Pat. No. 5,325,392
U.S. Pat. No. 5,936,994
U.S. Pat. No. 5,956,355
U.S. Pat. No. 6,104,739
U.S. Pat. No. 6,201,824
U.S. Pat. No. 6,617,188
U.S. Pat. No. 6,847,661 US20050035295
US patent application, Yan Zhou and Matthew J. Everett "Fourier domain optical coherence tomography employing a swept multi-wavelength laser and a multi-channel receiver" filed on Jul. 1, 2005, application Ser. No. 11/174,158

OTHER PUBLICATIONS

Amano, T. et al. (2005). "Optical frequency-domain reflectometry with a rapid wavelength-scanning superstructure-grating distributed Bragg reflector laser." Applied Optics 44(5): 808-816

Buss J. et al. (2005) "Tunable Laser Diodes and Related Optical Sources" Second Edition, John Wiley & Sons, Inc., Hoboken, N.J.

Choma, M. A. et al. (2003). "Sensitivity advantage of swept source and Fourier domain optical coherence tomography." Optics Express 11(18): 2183-2189

Hong, J. et al. (1998) "Enhanced Wavelength Tuning Range in Two-Section Complex-Coupled DFB Lasers by Alternating Gain and Loss Coupling", Journal of Lightwave Technology, 16(7): 1323

Hong, J. et al. (1999) "Cascaded strongly gain-coupled (SGC) DFB lasers with 15-nm continuous-wavelength tuning", Photonics Technology Letters, IEEE 11(10): 1214-1216.

Hong, J., et al. (1999) "Matrix-grating strongly gain-coupled (MC-SGC) DFB lasers with 34-nm continuous wavelength tuning range" Photonics Technology Letters, IEEE 11(5): 515-517.

Huber, R. et al. (2005). "Amplified, frequency swept lasers for frequency domain reflectometry and OCT imaging: design and scaling principles." Optics Express 13(9): 3513-3528

Huber, R., et al. (2006). "Fourier Domain Mode Locking (FDML): A new laser operating regime and applications for optical coherence tomography." Optics Express 14(8): 3225-3237

Muller, M. et al. (2003) "1.3-μm Continuously Tunable Distributed Feedback Laser With Constant Power Output Based on GaInNAs—GaAs", Photonics Technology Letters, IEEE 15(7) 897-899;

Mitsui T. (1999) "Dynamic Range of Optical Reflectometry with Spectral Interferometry." Japanese Journal of Applied Physics 38(10): 6133-6137

Oh, W. Y. et al. ("Wide tuning range wavelength-swept laser with two semiconductor optical amplifiers." Photonics Technology Letters, IEEE 17(3): 678-680

Thorlab Inc. Product Catalog, Vol. 17, (2005) page 469

T. van Caenegem et al, Progress in Crystal Growth and Characterization of Materials 35(2-4): 263-268 (1997)

We claim:

1. A swept source OCT system comprising:

a tunable light source;

a beam splitter for dividing the light along a sample and a reference path;

a photodetector for receiving light returned from both the sample and the reference paths and generating output signals as a function of time as the wavelength of the source is tuned;

a processor for analyzing the output signals to derive a reflectance distribution along the sample path and wherein the tunable light source includes an elongated optical waveguide structure, with one end thereof defining a laser output facet;

a linear series of distributed feedback gratings formed along the waveguide structure to define a series of resonant cavities;

a series of semiconductor gain structures formed within the waveguide structure and aligned with the gratings, with the bandgap energy of the gain structure increasing towards said output facet; and a power supply for supplying current to the gratings and the gain structures in a manner to generate laser output from each resonant cavity and for wavelength tuning the output.

2. An OCT system as recited in claim 1, wherein a common current is supplied to a grating and the associated gain structure.

3. An OCT system as recited in claim 1, wherein current is independently supplied to a grating and the associated gain structure.

4. An OCT system as recited in claim 1, wherein current is simultaneously supplied to all the gratings and the gain structures and wherein the current is tuned so that a tuned, multi-wavelength output is generated.

5. An OCT system as recited in claim 1, wherein current is supplied to the gain structure of each of the associated resonant cavities, said current being controlled in manner so that each of the gain sections are sequentially activated and tuned one at a time so that a tuned, narrow-band output is generated.

6. A method of evaluating the reflectance distribution within a sample using swept source OCT comprising the steps of:

providing a tunable light source, said light source including an elongated optical waveguide structure, with one end thereof defining a laser output facet, a linear series of distributed feedback gratings formed along the waveguide structure to define a series of resonant cavities, a series of semiconductor gain structures formed within the waveguide structure and aligned with the gratings, with the bandgap energy of the gain structures increasing towards said output facet, and a power supply for supplying current to the gratings and the gain structures in a manner to generate laser output from each resonant cavity and for wavelength tuning the output;

dividing the light along a sample and a reference path;

measuring light returned from both the sample and the reference paths and generating output signals as a function of time as the wavelength of the source is tuned; and analyzing the output signals to derive a reflectance distribution along the sample path and wherein the light source is operated by supplying current to the gratings and the gain structures in a manner to generate laser output from each resonant cavity and for wavelength tuning the output.

7. A method as recited in claim 6, wherein current is simultaneously supplied to all the gratings and the gain structures and wherein the current is tuned so that a tuned, multi-wavelength output is generated.

8. A method as recited in claim 6, wherein current is supplied to the gain structure of each of the associated resonant cavities, said current being controlled in manner so that each of the gain sections are sequentially activated and tuned one at a time so that a tuned, narrow-band output is generated.

* * * * *

UNITED STATES PATENT AND TRADEMARK OFFICE

CERTIFICATE OF CORRECTION

PATENT NO. : RE 41,633 E
APPLICATION NO. : 12/555622
DATED : September 7, 2010
INVENTOR(S) : Yan Zhou et al.

It is certified that error appears in the above-identified patent and that said Letters Patent is hereby corrected as shown below:

Title Page 1, in column 2, item (57) under "Abstract", line 7, delete "MWQs," and insert --MQWs,--, therefor.

On page 2, in column 1, item (56) under "Other Publications", line 5, "Three-dimenional" and insert --Three-dimensional--, therefor.

On page 2, in column 2, item (56) under "Other Publications", line 4, after "Müller" delete "ller".

In column 3, line 7, delete "GalnNAs" and insert --GaInNAs--, therefor.

In column 4, line 31, delete "MWQs" and insert --MQWs--, therefor.

In column 7, line 14, delete "GalnNAs" and insert --GaInNAs--, therefor.

In column 7, line 45, in claim 1, delete "structure" and insert --structures--, therefor.

Signed and Sealed this

Twenty-third Day of November, 2010

David J. Kappos

David J. Kappos
*Director of the United States Patent and Trademark Office*